US012057304B2

(12) United States Patent
Ovchinnikova et al.

(10) Patent No.: US 12,057,304 B2
(45) Date of Patent: Aug. 6, 2024

(54) CORRELATIVE MULTIMODAL CHEMICAL IMAGING VIA MACHINE LEARNING

(71) Applicant: UT-Battelle, LLC, Oak Ridge, TN (US)

(72) Inventors: Olga S. Ovchinnikova, Oak Ridge, TN (US); Anton V. Ievlev, Oak Ridge, TN (US); Matthias Lorenz, Toronto (CA); Nikolay Borodinov, Newtown, PA (US); Steven T. King, Hempstead, NY (US)

(73) Assignees: UT-Battelle, LLC, Oak Ridge, TN (US); University of Tennessee Research Foundation, Knoxville, TN (US)

( * ) Notice: Subject to any disclaimer, the term of this patent is extended or adjusted under 35 U.S.C. 154(b) by 492 days.

(21) Appl. No.: 17/337,919

(22) Filed: Jun. 3, 2021

(65) Prior Publication Data

US 2021/0384021 A1 Dec. 9, 2021

Related U.S. Application Data

(60) Provisional application No. 63/034,829, filed on Jun. 4, 2020.

(51) Int. Cl.
*H01J 49/00* (2006.01)
*G01N 23/2258* (2018.01)
(Continued)

(52) U.S. Cl.
CPC ...... *H01J 49/0036* (2013.01); *G01N 23/2258* (2013.01); *G06N 5/04* (2013.01);
(Continued)

(58) Field of Classification Search
CPC .. H01J 49/0036; H01J 49/0004; H01J 49/164; G01N 23/2258; G01N 2223/07;
(Continued)

(56) References Cited

U.S. PATENT DOCUMENTS

2015/0131888 A1* 5/2015 Caprioli ............... G06F 18/28
382/133

OTHER PUBLICATIONS

Van De Plas, R. et al., "Image fusion of mass spectrometry and microscopy: a multimodality paradigm for molecular tissue mapping", Nat Methods, Apr. 2015, pp. 366-372, vol. 12, No. 4.
(Continued)

*Primary Examiner* — Roy Y Yi
*Assistant Examiner* — Geoffrey T Evans
(74) *Attorney, Agent, or Firm* — Scully, Scott, Murphy & Presser, P.C.

(57) ABSTRACT

Machine learning approach can combine mass spectral imaging (MSI) techniques, one with low spatial resolution but intact molecular spectra and the other with nanometer spatial resolution but fragmented molecular signatures, to predict molecular MSI spectra with submicron spatial resolution. The machine learning approach can perform transformations on the spectral image data of the two MSI techniques to reduce dimensionality, and using a correlation technique, find relationships between the transformed spectral image data. The determined relationships can be used to generate MSI spectra of desired resolution.

29 Claims, 7 Drawing Sheets
(2 of 7 Drawing Sheet(s) Filed in Color)

(51) Int. Cl.
  *G06N 5/04* (2023.01)
  *G06N 20/00* (2019.01)
  *H01J 49/16* (2006.01)
(52) U.S. Cl.
  CPC .......... *G06N 20/00* (2019.01); *H01J 49/0004* (2013.01); *H01J 49/164* (2013.01); *G01N 2223/07* (2013.01); *G01N 2223/40* (2013.01)
(58) Field of Classification Search
  CPC ...... G01N 2223/40; G06N 5/04; G06N 20/00; G16C 20/20; G16C 20/70
  See application file for complete search history.

(56) References Cited

OTHER PUBLICATIONS

Spiteri, M. et al., "Data fusion between high resolution 1H-NMR and mass spectrometry: a synergetic approach to honey botanical origin characterization", Anal Bioanal Chem., 2016, pp. 4389-4401, vol. 408.

Vollnhals, F. et al., "Correlative Microscopy Combining Secondary Ion Mass Spectrometry and Electron Microscopy: Comparison of Intensity-Hue-Saturation and Laplacian Pyramid Methods for Image Fusion", Anal. Chem., 2017, pp. 10702-10710, vol. 89.

Fisher, G. et al., "A New Method and Mass Spectrometer Design for TOF-SIMS Parallel Imaging MS/MS", Anal. Chem., 2016, pp. 6433-6440, vol. 88.

Ievlev, A. et al., "Nanoscale Electrochemical Phenomena of Polarization Switching in Ferroelectrics", ACS Appl. Mater. Interfaces, 2018, pp. 38217-38222, vol. 10.

Ievlev, A. et al., "Automated Interpretation and Extraction of Topographic Information from Time of Flight Secondary Ion Mass Spectrometry Data", Sci. Rep., 2017, pp. 1-7, vol. 7, No. 17099.

Ovchinnikova, O. et al., "Co-registered Topographical, Band Excitation Nanomechanical, and Mass Spectral Imaging Using a Combined Atomic Force Microscopy/Mass Spectrometry Platform", ACS Nano, 2015, pp. 4260-4269, vol. 9, No. 4.

Ievlev, A. et al., "Non-conventional mechanism of ferroelectric fatigue via cation migration", Nat. Commun., 2019, pp. 1-8, vol. 10, No. 3064.

* cited by examiner

CORRELATIVE MULTIMODAL CHEMICAL IMAGING VIA MACHINE LEARNING

CROSS-REFERENCE TO RELATED APPLICATIONS

This application claims the benefit of U.S. Provisional Application No. 63/034,829, filed on Jun. 4, 2020, which is incorporated by reference herein in its entirety.

STATEMENT REGARDING FEDERALLY SPONSORED RESEARCH OR DEVELOPMENT

This invention was made with Government support under DE-AC05-00OR22725 awarded by US Department of Energy. The Government has certain rights to this invention.

FIELD

The present application relates generally to computers and computer applications, machine learning, chemical imaging, spectrometry, and more particularly to correlative multimodal chemical imaging via machine learning.

BACKGROUND

Chemical imaging such as mass spectrometry imaging (MSI) enables characterization of chemical compositions in a wide range of systems such as biological tissues, functional nanomaterials and polymer blends. For example, mass spectrometry imaging (MSI) can aid in investigating chemical nature of complex systems, providing the ability to simultaneously identify components and pinpoint their distribution across a sample. Many fields of study can benefit from chemical visualization at high spatial resolution e.g., sub-micron spatial resolutions. However, achieving the necessary high spatial resolution to distinguish chemical differences between individual components and generating intact component spectra is still a challenge with any single imaging approach. While mass spectrometry imaging approaches with high resolution are being developed, the combination of spatial and spectral limitations of the existing techniques makes this direct measurement at high spatial resolutions practically infeasible.

BRIEF SUMMARY

The summary of the disclosure is given to aid understanding of a device, computer system and/or method of correlative multimodal chemical imaging via machine learning, and not with an intent to limit the disclosure or the invention. It should be understood that various aspects and features of the disclosure may advantageously be used separately in some instances, or in combination with other aspects and features of the disclosure in other instances. Accordingly, variations and modifications may be made to the computer system and/or their method of operation to achieve different effects.

In an aspect, a system can include an instrument configured to acquire first-type spectral image data, the first-type spectral image data corresponding to a first-type spectral-data cube having two spatial dimensions of first-spatial resolution and one spectral dimension, where each point in the two spatial dimensions has an associated first-type spectrum, the first-type spectral-data cube indicative of one or more constitutive molecular compounds of a sample and their abundance on the sample's surface corresponding to the two spatial dimensions. The instrument can also be configured to acquire second-type spectral image data, the second-type spectral image data corresponding to a second-type spectral-data cube having two spatial dimensions of second-spatial resolution and one spectral dimension, where each point in the two spatial dimensions has an associated second-type spectrum, the second-type spectral-data cube indicative of fragments of the one or more constitutive molecular compounds of the sample and their abundance on the sample's surface corresponding to the two spatial dimensions, the second-spatial resolution having higher-spatial resolution than the first-spatial resolution. The system can also include a processor configured to train a machine learning model. The processor can be configured to train the machine learning model by co-registering the first-type spectral-data cube and the second-type spectral data cube and spatially down-sampling the second-type spectral-data cube to the first-spatial resolution of the received first-type spectral-data cube. The processor can be configured to train the machine learning model also by transforming the first-type spectral-data cube into abundance maps of first components, where a first component of the first components includes one or more molecular compounds that coexist together spatially. The processor can be configured to train the machine learning model also by transforming the second-type spectral-data cube into abundance maps of second components, where a second component of the second components includes one or more fragments of one or more molecular compounds that coexist together spatially. The processor can be configured to train the machine learning model also by spatially correlating the first components' abundance maps with the second components' abundance maps, and storing resulting set of correlations as learned parameters of the machine learning model. The processor can be further configured to receive a new second-type spectral-data cube having the second-spatial resolution. The processor can be further configured to generate, based on the trained machine learning model, a first-type spectral data cube having the second-spatial resolution and corresponding to the newly received second-type spectral-data cube.

In another aspect, a system can include a processor and a memory device coupled with the processor. The processor can be configured to receive a first-type spectral-data cube having two spatial dimensions of first-spatial resolution and one spectral dimension, where each point in the two spatial dimensions has an associated first-type spectrum, where the first-type spectral-data cubes is indicative of one or more constitutive molecular compounds of a sample and their abundance on the sample's surface corresponding to the two spatial dimensions. The processor can also be configured to receive a second-type spectral-data cube having two spatial dimensions of second-spatial resolution and one spectral dimension, where each point in the two spatial dimensions has an associated second-type spectrum, where the second-type spectral-data cube is indicative of fragments of the one or more constitutive molecular compounds of the sample and their abundance on the sample's surface corresponding to the two spatial dimensions, the second-spatial resolution having higher-spatial resolution than the first-spatial resolution. The processor can also be configured to train a machine learning model. The processor can be configured to train the machine learning model by co-registering the first-type spectral-data cube and the second-type spectral data cube and spatially establishing one-to-one pairing of the spectra of the first-type spectral-data cube and the second-type spectral data cube. The processor can be configured to train the machine learning model also by transforming the first-type spectral-data cube into abundance maps of first components, where a first component of the first components includes one or more molecular compounds that coexist together spatially. The processor can be configured to train the machine learning model also by transforming the second-type spectral-data cube into abundance maps of second components, where a second component of the second components includes one or more fragments of one or more molecular compounds that coexist together spatially. The processor can be configured to train the machine learning model also by spatially correlating the first components' abundance maps with the second components' abundance maps, and storing resulting set of correlations as learned parameters of the machine learning model.

A computer-implemented method, in one aspect, can include receiving a first-type spectral-data cube having two spatial dimensions of first-spatial resolution and one spectral dimension, where each point in the two spatial dimensions has an associated first-type spectrum, where the first-type spectral-data cubes is indicative of one or more constitutive molecular compounds of a sample and their abundance on the sample's surface corresponding to the two spatial dimensions. The method can also include receiving a second-type spectral-data cube having two spatial dimensions of second-spatial resolution and one spectral dimension, where each point in the two spatial dimensions has an associated second-type spectrum, where the second-type spectral-data cube is indicative of fragments of the one or more constitutive molecular compounds of the sample and their abundance on the sample's surface corresponding to the two spatial dimensions, the second-spatial resolution having higher-spatial resolution than the first-spatial resolution. The method can also include training a machine learning model. Training the machine learning model can include co-registering the first-type spectral-data cube and the second-type spectral data cube and spatially down-sampling the second-type spectral-data cube to the first-spatial resolution of the received first-type spectral-data cube. Training the machine learning model can also include transforming the first-type spectral-data cube into abundance maps of first components, where a first component of the first components includes one or more molecular compounds that coexist together spatially. Training the machine learning model can also include transforming the second-type spectral-data cube into abundance maps of second components, where a second component of the second components includes one or more fragments of one or more molecular compounds that coexist together spatially. Training the machine learning model can also include spatially correlating the first components' abundance maps with the second components' abundance maps, and storing resulting set of correlations as learned parameters of the machine learning model. The method can also include receiving a new second-type spectral-data cube having the second-spatial resolution. The method can also include generating, based on the trained machine learning model, a first-type spectral data cube having the second-spatial resolution and corresponding to the newly received second-type spectral-data cube.

A computer readable storage medium storing a program of instructions executable by a machine to perform one or more methods described herein also may be provided.

Further features as well as the structure and operation of various embodiments are described in detail below with reference to the accompanying drawings. In the drawings, like reference numbers indicate identical or functionally similar elements.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

DETAILED DESCRIPTION

Machine learning systems and methods are disclosed, which can infer high-spatial resolution molecular or component spectra. A machine learning approach in an embodiment combines images from two mass spectrometry imaging (MSI) techniques providing different information, to predict molecular MSI spectra with high spatial resolution, e.g., submicron spatial resolution.

An example of one MSI technique, which a methodology disclosed herein combines, provides low spatial resolution but intact molecular spectra and an example of another MSI technique, which the methodology disclosed herein combines, provides nanometer spatial resolution but fragmented molecular signatures. The machine learning approach in an embodiment can incorporate known relations between the two, which produce different information about the chemical composition of the sample due to the difference in physical nature of the imaging methods. For example, the machine learning approach can provide for the automated prediction of molecular mass spectra with sub-micrometer spatial resolution by incorporating known relations between two imaging techniques.

Figure 1:
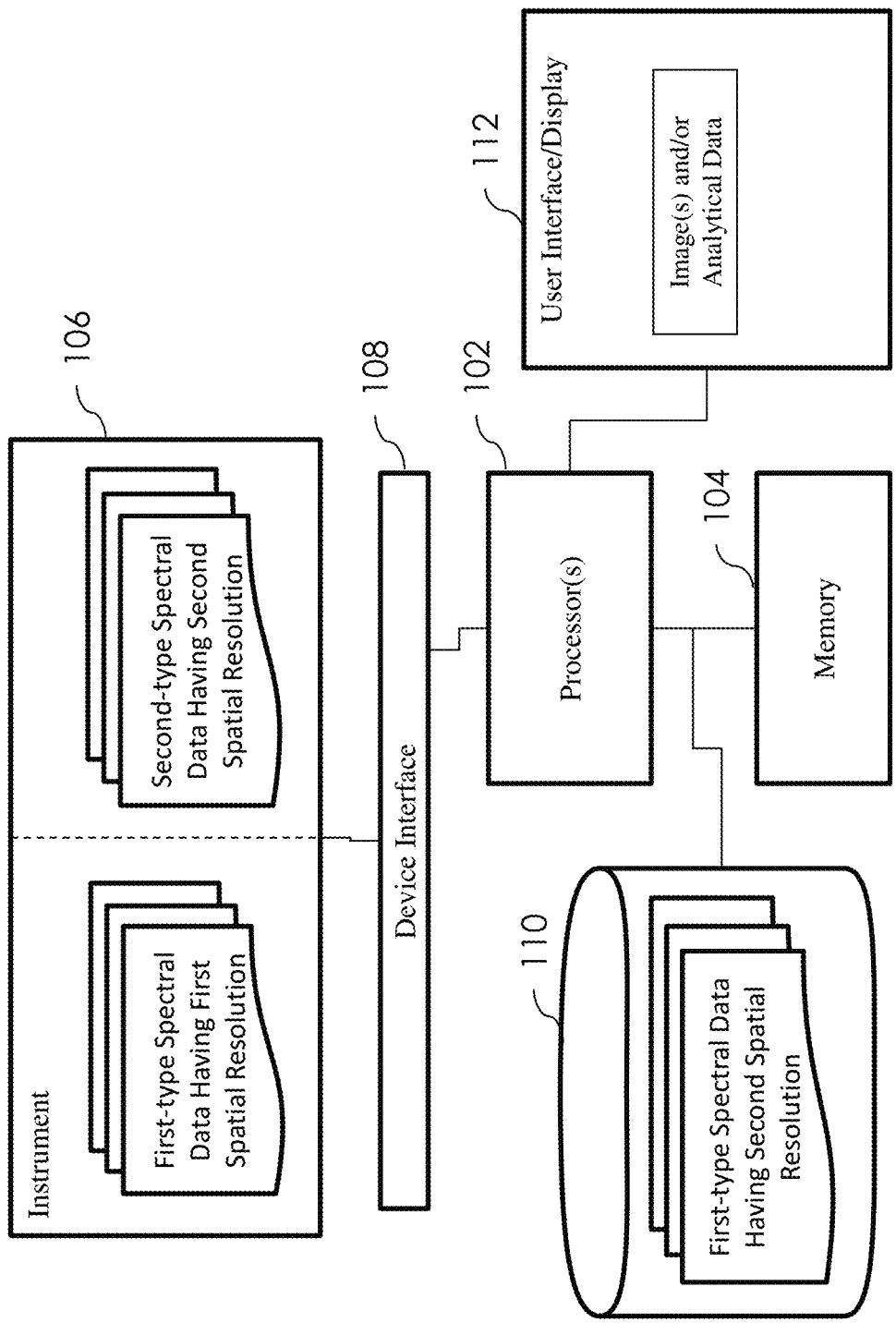
FIG. 1 is a diagram illustrating components of a machine learning system in an embodiment.

FIG. 1 is a diagram illustrating components of a machine learning system in an embodiment. The components shown include computer-implemented components, for instance, implemented and/or run on one or more hardware processors, or coupled with one or more hardware processors. One or more hardware processors, for example, may include components such as programmable logic devices, microcontrollers, memory devices, and/or other hardware components, which may be configured to perform respective tasks described in the present disclosure. Coupled memory devices may be configured to selectively store instructions executable by one or more hardware processors. A processor 102, e.g., a hardware processor, may be a central processing unit (CPU), a graphics processing unit (GPU), a field programmable gate array (FPGA), an application specific integrated circuit (ASIC), another suitable processing component or device, or one or more combinations thereof. The processor may be coupled with a memory device 104. The memory device may include random access memory (RAM), read-only memory (ROM) or another memory device, and may store data and/or processor instructions for implementing various functionalities associated with the methods and/or systems described herein. The processor may execute computer instructions stored in the memory or received from another computer device or medium.

The processor 102 may be coupled with an instrument 106 which includes a spectrometer capable of acquiring spectral image data of a sample, e.g., via a device interface or the like 108. Such spectral image data can correspond to a data cube having two spatial dimensions (e.g., x-y plane coordinate) and one spectral dimension (spectral information about the sample at a spatial point). For instance, an acquired spectral image can be transformed into such a data cube for computer data processing. In an embodiment, the instrument 106 can have a spectrometer capable of taking two different types of spectral images. In another embodiment, the instrument 106 can have multiple spectrometers, one capable of taking spectral images of one type, and another capable of taking spectral images of another type. In an embodiment, the processor 102 and the instrument 106 can be integrated in one device. In another embodiment, the processor 102 and the instrument 106 can be separate devices communicatively coupled to one another.

The processor 102 can receive a first-type spectral-data cube having two spatial dimensions of first-spatial resolution and one spectral dimension. Each point in the two spatial dimensions has an associated first-type spectrum. The first-type spectral-data cube is indicative of one or more constitutive molecular compounds of a sample and their abundance on the sample's surface corresponding to the two spatial dimensions.

The processor 102 can also receive a second-type spectral-data cube having two spatial dimensions of second-spatial resolution and one spectral dimension. Each point in the two spatial dimensions has an associated second-type spectrum. The second-type spectral-data cube is indicative of fragments of the one or more constitutive molecular compounds of the sample and their abundance on the sample's surface corresponding to the two spatial dimensions. The second-spatial resolution has higher-spatial resolution than the first-spatial resolution.

In an embodiment, the instrument 106 includes a spectrometer capable of acquiring matrix-assisted laser desorption/ionization (MALDI) imaging signals having first-spatial resolution and a spectrometer capable of acquiring time-of-flight secondary ion mass spectrometry (ToF-SIMS) imaging signals having second-spatial resolution. In another embodiment, the instrument 106 can include a spectrometer capable of acquiring matrix-assisted laser desorption/ionization (MALDI) imaging signals having first-spatial resolution, and capable of acquiring time-of-flight secondary ion mass spectrometry (ToF-SIMS) imaging signals having second-spatial resolution.

In an embodiment, the first-type spectral-data cube is a MALDI-MS image, and the first-type spectrum is MALDI-MS spectrum, and the second-type spectral-data cube is ToF-SIMS image, and the second-type spectrum is ToF-SIMS spectrum. For instance, the first-spatial resolution corresponds to 5-50 µm and the second-spatial resolution corresponds to 0.05-1 µm, per point of the two spatial dimensions.

For example, the machine learning approach can provide for the automated prediction of molecular mass spectra with sub-micrometer spatial resolution by incorporating known relations between matrix-assisted laser desorption/ionization (MALDI) and time-of-flight secondary ion mass spectrometry (ToF-SIMS) signals. In MALDI, analyte species are mixed with a matrix compound that facilitates primary charge carrier formation upon laser irradiation. Charge transfer from the matrix to the analyte molecule enables the preservation of a singly charged intact molecular species for identification. At the same time, the use of laser ionization in standard commercially available geometries limits the spatial resolution to 5-50 µm. In contrast, ToF-SIMS uses focused ion beams to release secondary ions from analyte species, enabling sub-micrometer spatial resolutions but resulting in significant fragmentation of molecular compounds, which can complicate the interpretation of mass spectra. The combination of both techniques offers the opportunity for complementary information, enabling predictive chemical imaging of intact molecular species with sub-micrometer spatial resolution, which can aid in research advancement in various fields. For example, the machine learning approach can enable chemical imaging of molecular information provided by MALDI with sub-micrometer spatial resolution of ToF-SIMS, allowing for chemical characterization at a sub-micrometer spatial resolution. In an embodiment, the known relationships, e.g., physical relationships, between the two MSI channels of information can be enforced via a machine-learning approach to generate intact molecular MALDI-type spectra and chemical maps at ToF-SIMS resolution in imaging a sample. In an embodiment, the machine learning approach can be adopted for other types of imaging, e.g., incorporate other channels of information and/or reconstruction constraints, e.g., where physical relationships between methods can be considered, e.g., and cross correlating and/or performing combinatorial processing of the captured signals.

The processor 102 can train a machine learning model to automate the combination of the two spectral types of image datasets to predict the distribution of molecular species with sub-micrometer spatial resolution. Given a previously unseen or new data cube representing an image of the second-type spectrum or spectra, the trained machine learning model can predict or generate an image of the first-type spectrum or spectra having spatial resolution of the second-type spectrum. By way of example, given a data set or data cube of a new ToF-SIMS image, the trained machine learning model can predict or generate a corresponding a MALDI image with ToF-SIMS image's spatial resolution.

Training the machine learning model can include the processor 102 performing the following: co-registering the first-type spectral-data cube and the second-type spectral data cube, spatially establishing one-to-one pairing of the spectra of first-type spectral-data cube and the second-type spectral data cube, for example, by spatially down-sampling the second-type spectral-data cube to the first-spatial resolution of the received first-type spectral-data cube, transforming the first-type spectral-data cube into abundance maps of first components, where a first component of the first components includes one or more molecular compounds that coexist together spatially, transforming the second-type spectral-data cube into abundance maps of second components, where a second component of the second components includes one or more fragments of one or more molecular compounds that coexist together spatially. Training the machine learning model can also include the processor 102 spatially correlating the first components' abundance maps with the second components' abundance maps, and storing resulting set of correlations as learned parameters of the machine learning model.

For example, the second-type spectral-data cube can be down-sampled to the spatial resolution of the first-type spectral-data cube by keeping every i-th data, by interpolation or by any other method to match the spatial resolutions of image data or spectra. In another embodiment, the resolutions of the two types of spectral-data cube can be matched by up-sampling the data with lower resolution to that of the data with higher resolution.

In an embodiment, the processor 102 may co-register the first-type spectral-data cube and the second-type spectral data cube by spatially linking the first-type spectral cube and the second-type spectral data cube by aligning coordinates of the two spatial dimensions of the first-type spectral cube and the second-type spectral data cube. In an embodiment, the processor 102 may align the coordinates of the two spatial dimensions of the first-type spectral cube and the second-type spectral data cube based on locating a marker or a set of markers appearing on the first-type spectral cubes. For example, the marker may be etched on the sample before taking an image of the sample. A marker can serve as an anchor for aligning the two images or image data represented by the first-type spectral-data cube and the second-type spectral data cube.

The processor 102 can perform transformations of the first-type spectral-data cube and the second-type spectral-data cube (e.g., which is down-sampled to match the spatial resolution of the first-type spectral-data cube). The transformation reduces the data dimensionality of the data cubes. For example, the processor 102 can transform the first-type spectral-data cube into abundance maps of first components, where a first component of the first components includes one or more molecular compounds that coexist together spatially. The processor 102 can also transform the second-type spectral-data cube (e.g., matching the spatial resolution of the first-type-spectral data cube) into abundance maps of second components, where a second component of the second components includes one or more fragments of one or more molecular compounds that coexist together spatially.

For instance, the processor 102 can decompose first spectra of the first-type spectral-data cube as linear combinations of spectra corresponding to the first components and determine the first components' abundance maps as the first spectra's weights associated with the first components. The processor 102 can also decompose second spectra of the second-type spectral-data cube as linear combinations of spectra corresponding to the second components and determine the second components' abundance maps as the second spectra's weights associated with the second components. In an embodiment, decomposing can include performing a non-negative matrix factorization (NMF).

In an embodiment, the processor 102 can reduce data dimensionality using non-negative matrix factorization (NMF). In an aspect, NMF assumes that each mass spectrum in each point can be represented as a linear combination of a small number of archetypical non-negative spectra referred to as endmembers, with weights forming abundance maps of the spatial distribution. For NMF, the dataset (e.g., first-type spectral-data cube or second-type spectral-data cube) can be represented as a linear combination of a series of archetypical spectra (Equation 1):

$$V = W \times H + R \quad (1)$$

where V is the original data with the shape m×n (m is the number of spatial points, n is the length of the mass spectra); W is matrix of weights with size of m×p; H is a matrix of archetypical spectra with size of p×n, (p is number of components); and R is a residual matrix. For NMF, every element (e.g., $a_{ij}$) of the data matrix V (m rows and n columns) is greater than or equal to zero ($a_{ij} \geq 0$). NMF finds matrices W (m rows and p columns) and H (p rows and n columns), and every element of W and H is greater than or equal to zero. In an embodiment, p can be predefined or given. For example, in an embodiment, p can be set to 20. Generally, NMF iteratively modifies the initial values of W and H so that the product approaches V. NMF can terminate when the approximation error converges or when a predefined number of iterations $I_{max}$ is reached. By way of example, W and H matrices may be determined by minimizing the Frobenius norm, e.g., minimizing $\|V - WH\|^2$. Other approaches can be used to find W and H in NMF.

Figure 3:
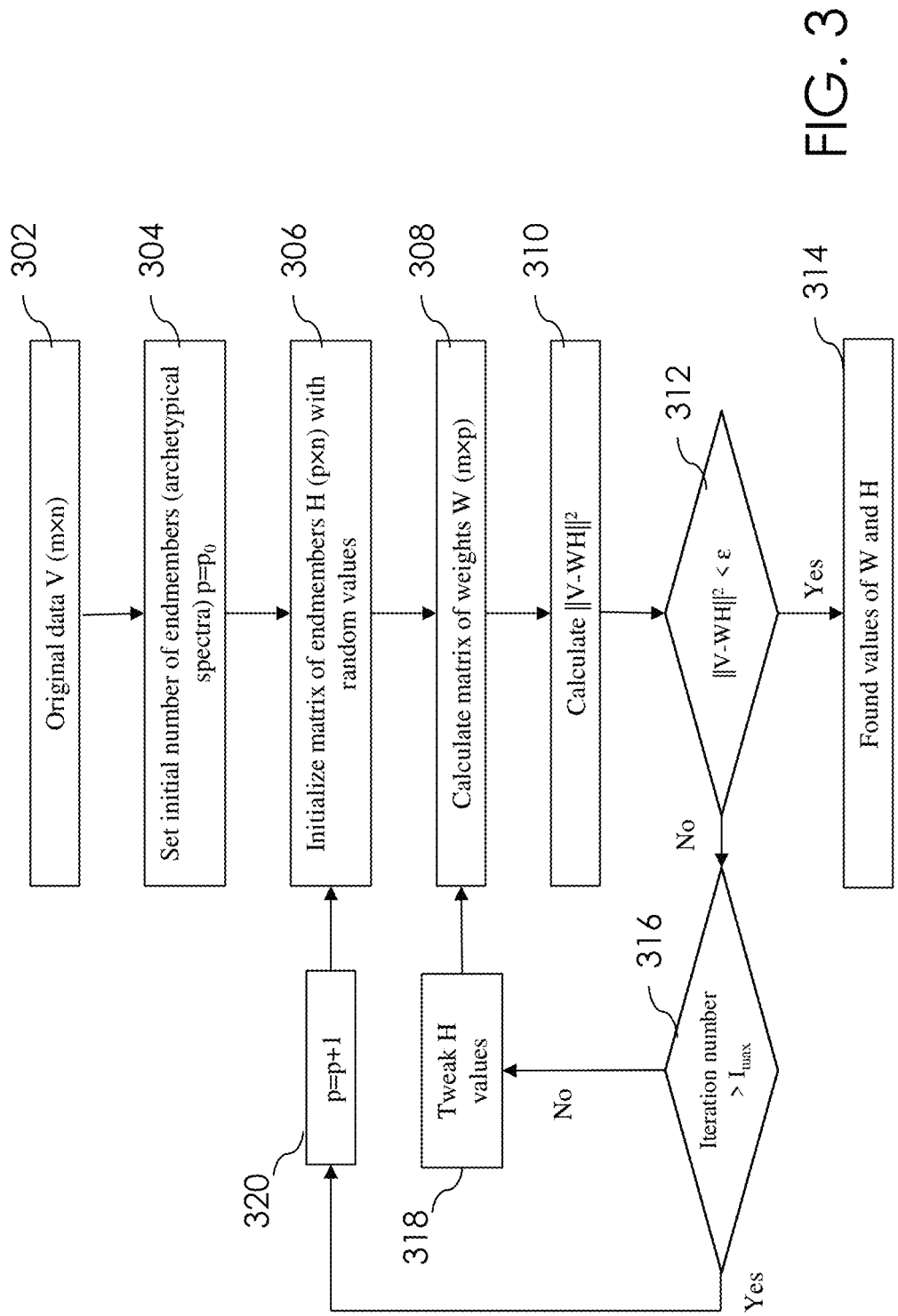
FIG. 3 is a flow diagram illustrating a method of NMF.

By way of example, FIG. 3 shows an NMF method in an embodiment. At 302, a processor may receive data, for example matrix V of m rows and n columns (m×n), where m is the number of spatial points, n is the length of the mass spectra. At 304, the processor may set initial number of endmembers (archetypical spectra), e.g., set p to $p_0$. The initial number (or $p_0$) can be a predefined or configured. For example, p can be set initially to 20 or another number. At 306, the processor may initialize the matrix of endmembers H of p rows and n columns (p×n) with random values. The processor may also initialize a number of iterations to 1. At 308, the processor may compute matrix of weights, W of m rows and p columns (m×p), given V and H. At 310, the processor may compute $\|V - WH\|^2$. At 312, the processor determines whether the computation at 310 is less than a threshold, e.g. an approximation error C. Such approximation error can be predefined or configured. At 314, if the computation at 310 is less than the threshold, it is determined that W and H are found. Otherwise at 316, the processor determines whether the number of iterations is less than a maximum number of iterations. The maximum number of iterations can be predefined or configured. At 318, if the number of iterations is not greater than the max number of iterations, the processor may alter or change values of H with different one or more random values. Then the logic may continue to 308 and repeat. At 320, if the number of iterations is greater than the maximum number of iterations, the number of endmembers can be changed, for example, incremented by one. The number of iterations can be reset to 1. Then the logic may proceed to 306 and repeat.

The maps of corresponding weights W are further referred to as abundance maps. There can be an abundance map per component or endmember. In an embodiment, the NMF algorithm seeks to decrease the reconstruction error R given the amount to components and simultaneously enforces its non-negativity. The latter lies in perfect agreement with the nature of mass spectrometry data. Under this model, the random shots cannot be fit by NMF decomposition and are cast out into the residual matrix R. This allows to preserve the spatial details while improving signal-to-noise ratio. In an aspect, one NMF component does not necessarily contain one compound but rather a mixture of compounds that spatially coexists and cannot by separated by linear unmixing. For example, if compounds A and B always appear together in the tissue, their spectra will appear in the same component as well. Performing NMF on each of the first-type spectral-data cube and the second-type spectral-data cube simplifies both datasets to a number of endmembers and corresponding abundance maps.

In an embodiment, the processor 102 determines some physical constraints and correlations, for reconstruction, as a relationship between the second type (e.g., ToF-SIMS) and first type (e.g., MALDI) point spectra. In an embodiment, it can be assumed the following: 1) each compound in the sample has a specific localization independent on imaging technique, 2) those compounds have characteristic non-negative second type (e.g., ToF-SIMS) and first type (e.g., MALDI) spectra for the chosen two type sample preparation conditions, 3) the mass spectrum in each point represents a linear combination of mass spectra of all compounds presented in this point. The processor 102, e.g., based on these assumptions, can enforce linearity on the data transformation relating the information gathered from the second type signals (e.g., ToF-SIMS) and the first type signals (e.g., MALDI).

The processor 102 can spatially correlate the first components' abundance maps with the second components' abundance maps, and store a resulting set of correlations as learned parameters of the machine learning model. In an embodiment, spatially correlating the abundance maps can include performing a canonical correlation analysis to determine the resulting set of correlations.

For example, to identify relations between the first-type spectral-data cube and the second-type spectral-data cube, the processor 102 may utilized canonical correlation analysis (CCA). This algorithm looks to maximize the correlation between two column vectors X and Y, with length p each, by identifying two vectors $a_1$ and $b_1$ in such a way that correlation between $a_1^T \times X$ and $b_1^T \times Y$ is maximized, this gives first pair of canonical variables. Then the same algorithm is used to find second pair of canonical variables $a_2^T \times X$ and $b_2^T \times Y$ with a constraint, that are uncorrelated with the previous pairs of canonical variables. This procedure can be continued up to p times, providing up to p pairs of canonical variables.

In an embodiment, the processor 102 uses first components' abundance maps and the second components' abundance maps, e.g., the abundance maps generated by NMF, to find the correlation. In particular, using NMF components instead of the full data allows to reduce the amount of noise in the data, in addition, the peaks with similar abundance can be combined into the same NMF component which helps to increase the influence of the peaks with unique spatial distribution. In an embodiment, each spatial point in NMF-transformed datasets can be characterized by a p-long vector showing the intensities of the abundance map in that point. For example, the second-type spectral-data cube (e.g., ToF-SIMS NMF) loading (e.g., abundance maps) are used as X and the first-type spectral-data cube (e.g., MALDI) loading (e.g., abundance maps) are used as Y in the CCA. Both vectors X and Y have length of p. Performed CCA provides correlation weights matrices a and b, with shape of p×r each, where r is predefined number of canonical variables. r can be set equal to 10. The weight CCA matrices a and b show which linear mixture of the second-type spectral-data cube (e.g., ToF-SIMS NMF) components would correspond to which linear mixture of the first-type spectral-data cube (e.g., MALDI NMF).

The spatial correlation between the first-type spectral-data cube (e.g., MALDI) and the second-type spectral-data cube (e.g., ToF-SIMS NMF) abundance maps is used to identify the relationship between corresponding endmembers and, ultimately, the sample mass spectra in both modes. In an aspect, for each component (having one or more analyte compounds) present in the sample the localization of abundance maps is correlated between the two methods. In an example implementation embodiment, the processor 102 may use CCA with 10 components to link co-registered the second-type (e.g., ToF-SIMS) and the first-type (e.g., MALDI MSI) datasets or spectral-data cubes.

The processor 102 can also receive a new second-type spectral-data cube having the second-spatial resolution. The processor 102 can generate, based on the trained machine learning model, the first-type spectral-data cube having second-spatial resolution and corresponding to the newly received second-type spectral-data cube. For example, the processor 102 can transform the new second-type spectral-data cube having the second-spatial resolution into second-spatial resolution abundance maps of the second components, determine second-spatial resolution abundance maps of the first components from the stored resulting set of correlations and the second-spatial resolution abundance maps of the second components, and recover the first-type spectral-data cube having second-spatial resolution from the second-spatial resolution abundance maps of the first components.

In an embodiment, the processor 102 employing machine learning disclosed herein can predict high-spatial resolution molecular spectra. To achieve this, the processor 102 in an embodiment establishes the coefficients of all linear unmixing and linear combination operations which can be done during the training of the algorithm or machine learning model. The training can be performed on the co-registered the second-type spectral-data cube and the first-type spectral-data cube (e.g., ToF-SIMS and MALDI MSI datasets) brought to the same spatial resolution. These two datasets separately undergo dimensionality reduction (e.g., by NMF) to extract abundance maps which are then paired through a correlation algorithm establishing a set of correlations, e.g., CCA, establishing two matrices of CCA weights a and b, which contain information about the first-type and the second-type spectral data correlation (e.g., MALDI MSI and ToF-SIMS correlation). This set of correlations or matrix can be further used to reconstruct either of the dataset. For example, a first-type spectral data cube having the second-spatial resolution and corresponding to a newly received second-type spectral-data cube (having the second-spatial resolution) can be generated. For example, such set of correlations allows to infer MALDI-type molecular mass spectra by ToF-SIMS dataset at original high spatial resolution. For example, the newly received second-type spectral-data cube (e.g., new ToF-SIMS dataset) can be transformed by the NMF using previously calculated endmembers, then a trained CCA transformation infers the MALDI abundance maps via multiplication by the matrix G, which is followed by an inverse NMF which generates a MALDI-type mass spectral array at ToF-SIMS imaging resolution.

For example, transforming the new second-type spectral-data cube having the second-spatial resolution into second-spatial resolution abundance maps of the second components can include using the second components determined from the transforming of the second-type spectral-data cube into abundance maps of second components, e.g., the transforming having performed with a non-negative matrix factorization (NMF) on the second-type spectral-data cube. For instance, referring to Equation (1) above, given V (the new second-type spectral-data cube) and H (determined at previous transformation during training), W can be computed.

Recovering the first-type spectral-data cube having second-spatial resolution from the second-spatial resolution abundance maps of the first components can include performing an inverse CCA transformation, using weight matrices a and b, which provides corresponding first-type second-spatial resolution abundance maps (e.g., given a and b and X, find Y), which are used along with first-type components to restore first-type spectral-data cube. For example, referring to Equation (1) above, given W (from applying the trained correlation model) and H (known from previous transformation done at training), V can be computed as V=W×H.

The processor 102 can also be coupled with one or more storage devices 110, which can store data used by the processor in its processing. One or more storage devices 110 may store any other data. The generated or predicted data can also be stored on the storage device 110. A user interface and/or a display device 112, which may be coupled with the processor 102, may provide presentations such as images associated with the input spectral data and/or output spectral data, and/or any analytics performed on the spectral data.

In an embodiment, a processor performing the training and the reconstructing or generating using the trained model need not be the same processor. For instance, a processor may perform training of the machine learning model and another processor can use the trained machine learning model to predict or generate a new image.

Figure 2:
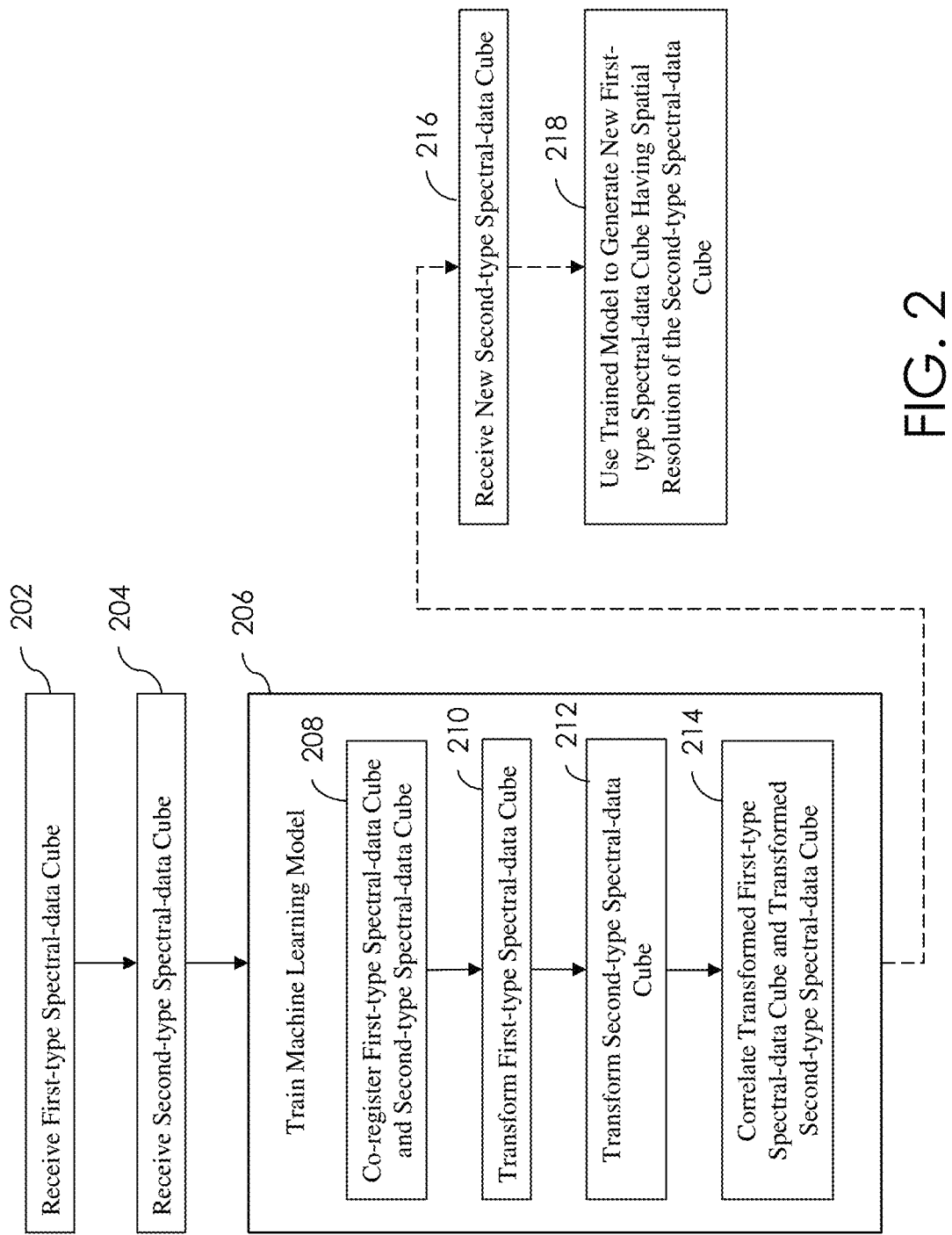
FIG. 2 is a flow diagram illustrating a machine learning method in an embodiment.

FIG. 2 is a flow diagram illustrating a machine learning method in an embodiment. One or more processors, e.g., hardware processors can perform the method in an embodiment. At 202, the method can include receiving a first-type spectral-data cube having two spatial dimensions of first-spatial resolution and one spectral dimension, where each point in the two spatial dimensions has an associated first-type spectrum, where the first-type spectral-data cubes is indicative of one or more constitutive molecular compounds of a sample and their abundance on the sample's surface corresponding to the two spatial dimensions. At 204, the method can include receiving a second-type spectral-data cube having two spatial dimensions of second-spatial resolution and one spectral dimension, where each point in the two spatial dimensions has an associated second-type spectrum, where the second-type spectral-data cube is indicative of fragments of the one or more constitutive molecular compounds of the sample and their abundance on the sample's surface corresponding to the two spatial dimension. The second-spatial resolution has different spatial resolution than the first-spatial resolution. In an embodiment, the second-spatial resolution has higher-spatial resolution than the first-spatial resolution.

The method can include training a machine learning model at 206 or machine learning. The training can include, at 208, co-registering the first-type spectral-data cube and the second-type spectral data cube, and e.g., spatially matching or corresponding the spatial-resolutions of the first-type spectral-data cube and the second-type spectral data cube, e.g., spatially establishing one-to-one pairing of the spectra of the first-type spectral-data cube and the second-type spectral data cube. For example, in an embodiment, in which the second-type spectral-data cube has higher-spatial resolution than the first-spatial resolution, the second-type spectral-data cube can be down-sampled to the first-spatial resolution of the received first-type spectral-data cube. Down-sampling can include keeping every i-th data, or another method.

The training can also include at 210, transforming the first-type spectral-data cube into abundance maps of first components, where a first component of the first components includes one or more molecular compounds that coexist together spatially. For instance, dimensionality of the first-type spectral-data cube can be reduced to first components, e.g., using NMF.

The training can further include at 212, transforming the second-type spectral-data cube into abundance maps of second components, where a second component of the second components includes one or more fragments of one or more molecular compounds that coexist together spatially. For instance, dimensionality of the second-type spectral-data cube can be reduced to second components, e.g., using NMF.

The training can further include at 214, spatially correlating the first components' abundance maps with the second components' abundance maps, and storing resulting set of correlations as learned parameters of the machine learning model.

At 216, the method can also include receiving a new second-type spectral-data cube having the second-spatial resolution. At 218, the method can include generating, based on the trained machine learning model, a first-type spectral data cube having the second-spatial resolution and corresponding to the newly received second-type spectral-data cube.

In another embodiment, a data cube with lower spatial resolution can be up-sampled to that of the data cube with higher spatial resolution. For instance, in this embodiment, the first-type spectral-data cube can be up-sampled to the second-spatial resolution of the received second-type spectral-data cube. Up-sampling can include interpolating the data. Thus, for example, matching of the spatial resolution can include down-sampling or up-sampling one or more of the second-type spectral-data cube and the first-type spectral-data cube.

The disclosed machine learning based approach for correlative chemical imaging allows reconstruction of spectral data with improved spatial resolution based on co-registered multimodal imaging. This approach can shine the light on the fine details of molecular distributions within complex systems and can be used, for example, for subcellular imaging of biological systems and incorporate other channels such as Raman and Fourier-transform infrared spectroscopy (FTIR) imaging considering that these systems also follow known mixing rules.

Figure 4:
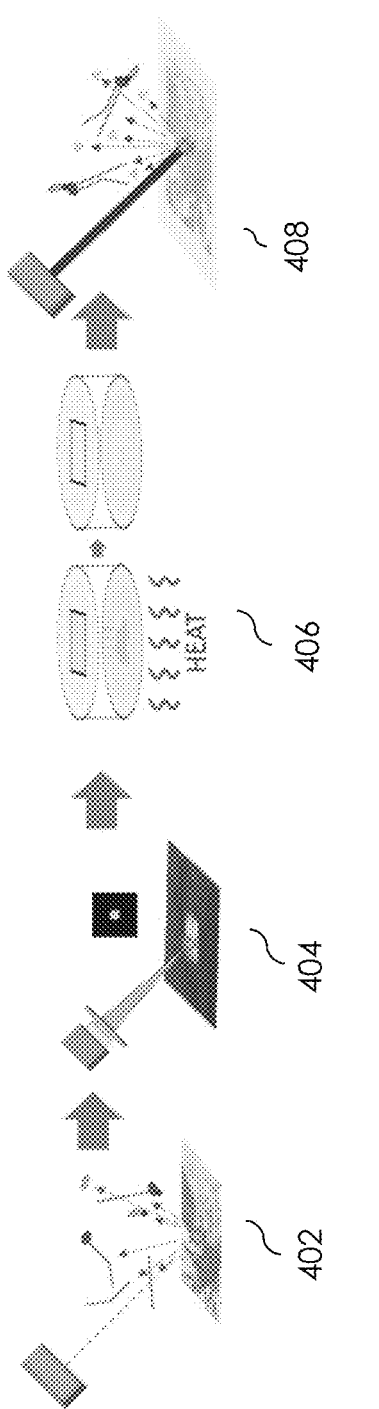
FIG. 4 illustrates image data acquisition and marking of a sample during acquisition of the data image in an embodiment.

The following description illustrates disclosed a system and/or method in one or more embodiments, using MALDI signals as an example for the first-type spectral-data cube and ToF-SIMS signals as an example for the second-type spectral-data cube. An example experiment can use a tissue sample for imaging and reconstruction. FIG. 4 illustrates image data acquisition and marking of a sample during acquisition of the data image in an embodiment. Acquisition of the second-type spectral data is shown at 402. Sputtering or etching of fiduciary markers is shown at 404. Application of a matrix is shown at 406. Acquisition of the first-type spectral data is shown at 408. The following describes the data acquisitions and marking in detail with reference to SIMS and MALDI imaging in an embodiment.

SIMS Imaging

In an example experiment, the Indium tin oxide (ITO)-coated glass slide having a tissue sample mounted thereon, can be mounted on top of a top mount sample holder for the ToF-SIMS instrument using electrically conductive carbon tape. A conductive pathway between the stage and the ITO surface of the slide can be confirmed by using a digital multimeter to gauge the resistance between the two surfaces. By way of example, a TOF.SIMS 5 secondary ion mass spectrometer can be used with a $B_{i3}^+$ primary ion beam (31 nA DC current). The instrument can be operated with maximum mass resolving power. Charge compensation can be enabled. Samples can be imaged in stage scan experiments, e.g., acquiring 5 shots per pixel with a pixel step size of 2 μm. The patched image of 10.9 mm×8.4 mm dimensions can be recorded.

Fiduciary Marker Etching

Three 250 μm×250 μm patches in the tissue can be milled using a SIMS $B_{i3}^+$ primary ion beam with 10% duty cycle, scanning 512×512 pixels in a sawtooth pattern. These patches can be located at the vertices of an imagined right triangle spanning the area of the tissue section. The locations of the etched markers can be obtained from the stage coordinates in the ToF-SIMS dataset with 10 nm precision. The MALDI imaging may allow the imaging of the markers with ca. 10 μm resolution.

Matrix Application and MALDI Imaging

The ITO-coated slide with two tissue samples on it can be scored and split in half using a handheld diamond-tipped glass cutter so that each half now bore one tissue sample section. The samples can then be gently cleaned with low-velocity dry air to remove glass particulate debris. A sublimation apparatus can be primed with 300 mg dry a-cyano-4-hydroxycinnamic acid powder and coupled to a rough vacuum pump. The sample's section can be mounted to the underside of the coolant reservoir of the apparatus with conductive copper tape. The apparatus can then be heated in a sand bath to 155° C., as measured by a digital thermometer probe placed into the sand bath directly beneath the apparatus, then maintained at a temperature between 150 and 160° C. for 20 minutes.

MALDI MSI data can be acquired using an instrument such as a spectrometer equipped with a laser and capable of acquiring MALDI MSI spectral image data. The tissue section can be sampled with a laser in a rectangular grid covering the entire tissue surface area with a pixel diameter of 50 μm. Each collected spectrum can be the sum of 500 laser shots randomly distributed within the 25 μm radius. Spectra can be collected on the mass range m/z (0-7300) using a digitizer frequency of 5 GHz, resulting in a spectral resolution of 246726 data points per spectrum. The resulting spectra can be individually normalized by total ion count (TIC) to account for pixel-to-pixel signal variation caused by the uneven distribution of CHCA matrix on the sample surface. Peaks of interest can be selected from the MALDI average spectrum. The analysis can be performed on a band of 60 manually identified peaks typically associated with low-mass lipids between m/z 500 and m/z 950.

MALDI and SIMS Co-Registration

Figure 7:
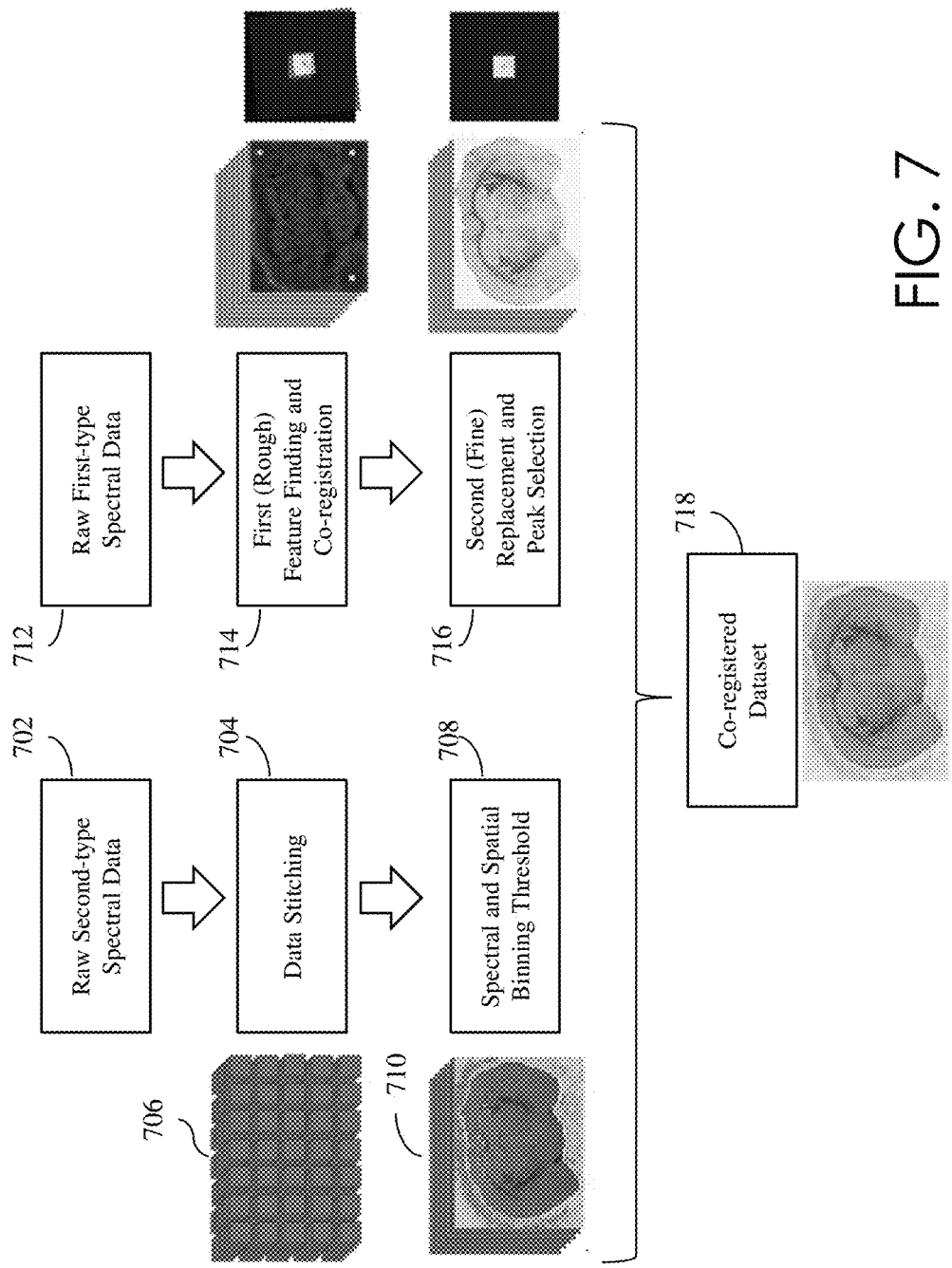
FIG. 7 shows an example of co-registration of two types of spectral data, for example, for MALDI and SIMS type of spectral data in an embodiment.

Generally, co-registering aligns or links the spatial coordinates of images the first-type spectral-data cube and the second-type spectral data cube. Co-registration can have different procedures for different types of spectral data. FIG. 7 shows an example of co-registration of two types of spectral data, for example, for MALDI and SIMS type of spectral data in an embodiment.

Data processing can be done using Python 3.6 or another computer-implemented language. Both the SIMS and MALDI datasets can be converted from different proprietary file formats into a common data structure. For example, Python codecs can be implemented for converting and merging these dissimilar data formats into the Universal Spectroscopic Imaging Data (USID) format, a file structure based on the Hierarchical Data File (HDF) format. For example, SIMS data 702 can be exported and formatted to files roughly constituting a chronologically ordered list of detected ions, their times-of-flight, and the pixel coordinates from which they originated. These data can be reformatted into spectral data of the format intensity-vs.-m/z with fixed m/z bin size, then saved as coordinate-linked lists of spectra. In an embodiment, data stitching of several field-of-view can be performed at 704 to produce data 706 that covers or approximates the size of the sample. By way of example, spectral (64×) binning on the SIMS dataset can be performed at 708 to reduce the on-disk size of the output file. MALDI data 712 can be exported, parsed to extract spectra into a dataset, and reformatted into USID format. By way of example, USID-formatted SIMS and MALDI data files can be co-registered by identifying ion maps within the MALDI dataset in which the etched fiduciary markers are visible as the dominant features of the map. Such maps can be identified and passed to a 2-part automated feature finding algorithm. A sliding window 2-dimensional (2D) correlation of the MALDI single ion images with the fiducial marker can be done to find the coarse position of the squares, e.g., as shown at 714. Since the size of the etched marker can be precisely known, the pixel dimension of the sliding window can be calculated with accuracy. The size of the sliding window step can be relatively high to speed up the feature finding as size matching makes it already very robust. A second stage in the co-registration algorithm can include fine adjustment of the scale, physical location and rotation of the image, e.g., as shown at 716. Through an iterative procedure maximizing the 2D correlation between the chosen marker shape and the local image, these parameters can be identified. The marker coordinates in MALDI dataset, as well as their counterpart coordinates within the SIMS dataset (as recorded during marker etching), can be saved as metadata attributes alongside their respective datasets within the merged USID data file. The linked pairs of coordinates therefore be quickly accessible for use in bidirectional co-registration of individual ion maps. An example of the co-registered dataset is shown at 718.

SIMS can be down-sampled to MALDI resolution via linear interpolation (or keeping only a subset, e.g., keeping only certain data) to establish one-to-one pairing of the spectra. The ionization for ToF-SIMS may lead to "salt-and-pepper" type of noise, a type of noise seen on images, as a certain number of secondary ions may be needed in order to get a representative spectrum. To co-register image A to image B, the stored pairs of marker coordinates can be read from the merged data file and used to calculate a 2×3 transformation matrix. This matrix specifies scaling, rotation, translation, and shearing parameters used to spatially transform the supplied coordinate pairs of image A into their corresponding coordinate pairs within image B. Once spatially aligned, image A can be passed through a linear interpolation filter to either up-sample or down-sample the image as necessary to match the resolution of image B. This results in a 1:1 translation of image A into the coordinate system of image B such that each pixel in the merged dataset now represents spatially-linked pairs of MALDI and SIMS spectra. This transformation may be performed bidirectionally, either co-registering image A to image B, or co-registering image B to image A. In an embodiment, the processing of raw MALDI and ToF-SIMS data may be performed on a high-performance computing cluster or cloud-based virtual machine. Such processing may also be on a single-core processor, or any other processor.

Processing of Co-Registered SIMS and MALDI Datasets

ToF-SIMS instrument allows stitching of several field-of-view allowing to cover the entire millimeter-sized sample. Within these discrete fields of view, individual pixels can be resolved by deflecting the ion beam to the analysis site using conventional ion optics. Near the edges of each field-of-view, the primary ion beam can be further deflected just prior to impacting the sample by the accumulated charge of the surface. This can result in the appearance of a grid-like artifact on the single ion maps which is not related to the distribution of the analytes in the sample. To reduce this distortion, the system and/or method in an embodiment can apply a 2D Fourier filter to decrease the intensity of the measurement artifacts. A 2D Gaussian smoothing can also be performed to eliminate the noise. In an embodiment, to extract knowledge out of the dataset or data cubes, the system and/or method can use non-negative matrix factorization (NMF).

In an embodiment, the generated image can be compared with the input new image, e.g., to check the quality of the predicted or generated image. For example, one or more metrics can be used to characterize the output of the spectral datasets: root mean square error (RMSE), spectral angle mapper (SAM), cross correlation (CC) and peak signal-to-noise ratio (PSNR). PSNR can be used to characterize the image compression quality and can be calculated as the ratio between the maximum possible power of a signal and the power of corrupting noise that affects the fidelity of its representation.

The disclosed system and/or method can be used to reconstruct spatial maps of any molecular species distribution with sub-micrometer spatial resolution under the conditions that they are visible in MALDI spectra and a reliable correlation of those peaks with signals in ToF-SIMS spectra can be found.

Figure 5:
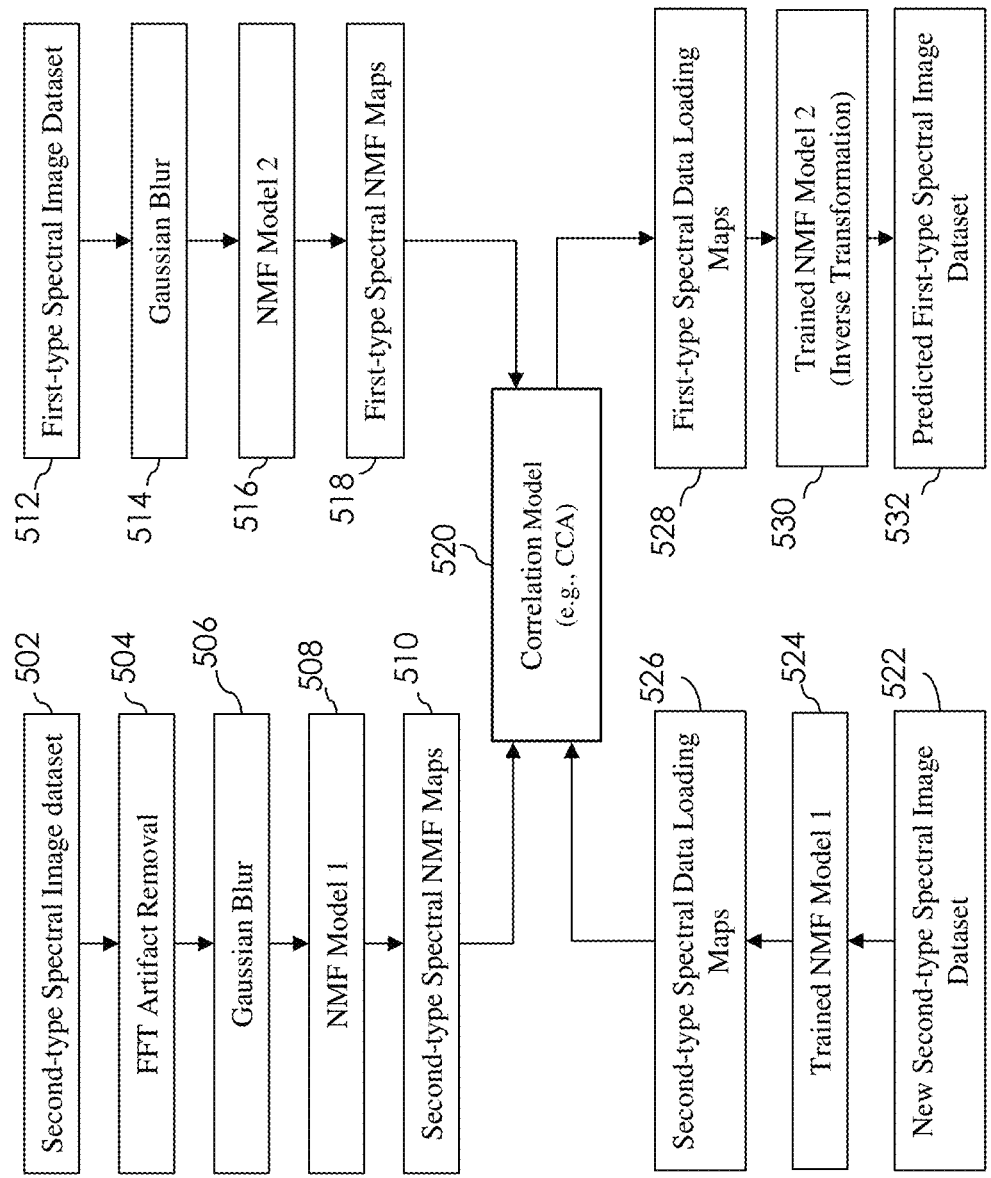
FIG. 5 is a flow diagram illustrating training of a machine learning model and using the model in an embodiment.

FIG. 5 is a flow diagram illustrating training of a machine learning model and using the model in an embodiment to generate a first-type spectral data cube having the second-spatial resolution, for example, generating high-spatial resolution molecular spectra. At 502, a dataset or data cube of second-type spectral data can be received. An example of such data can be SIMS image dataset. Image may be of a sample, such as a biological tissue or other material. At 504, filtering such as a Fast Fourier transform can be performed on the second-type spectral dataset or data cube to reduce distortion or remove artifacts. At 506, a smoothing technique such as a 2D Gaussian smoothing can be performed to eliminate noise in the second-type spectral dataset.

At 512, a dataset or data cube of first-type spectral data can be received. An example of such data can be MALDI image dataset. At 514, a smoothing technique such as a 2D Gaussian smoothing can be performed to eliminate noise in the first-type spectral dataset.

At 508 and 516, the two datasets, e.g., at the same spatial resolution, undergo dimensionality reduction. For example, at 508, a dimensionality reduction such as NMF can be performed to generate abundance maps 510 associated with the second-type spectral dataset. Similarly, at 516, a dimensionality reduction such as NMF can be performed to generate abundance maps 518 associated with the first-type spectral dataset. At 520, correlation algorithm correlates or links the abundance maps 510, 518. In an embodiment, a set of correlations (e.g., weights such as weight matrices a and b determined by CCA) generated by the correlation algorithm at 520 can be stored. The processing shown at 502-520 can be considered model training.

The trained model can be used to generate a new first-type spectral data or image, but having the spatial resolution of the second-type spectral data. For example, given a new SIMS dataset, a MALDI image dataset can be generated at the spatial resolution of the SIMS dataset, e.g., a desired reconstructed dataset of molecular intact species can be generated. At 522, a new second-type spectral dataset or data cube can be received. At 524, the new second-type spectral dataset transformed by the dimensionality reduction algorithm, e.g., NMF using endmembers or components already determined at 508. For example, given the known components, NMF can be used to find their abundance in the new second-type spectral dataset. This transformation generates or extracts abundance maps or loading maps 526 associated with the new second-type spectral dataset at higher spatial resolution. Using the CCA weight matrices a and b or correlation determined at 520 on the abundance maps or loading maps 526 associated with the new second-type spectral dataset, new abundance maps or loading maps 528 associated with the first-type spectral data at higher spatial resolution (e.g., resolution of the second-type spectral data) can be generated. For example, the trained correlation transformation at 520 can infer or predict the new abundance maps 528 associated with the first-type spectral data. At 530, an inverse transformation, e.g., the inverse of the transformation performed at 516 can generate the first-type spectral data at higher spatial resolution (e.g., resolution of the second-type spectral data) 532. For instance, given the new abundance map 528, weights of the components can be identified and used in Equation (1) above, to generate the first-type spectral data.

For example, the method in an embodiment can establish the coefficients of all linear unmixing (e.g., at 508 and 516) and linear combination (e.g., at 520) operations which is done during the training step of the algorithm. By way of example, this training step can be performed on the co-registered ToF-SIMS and MALDI MSI datasets brought to the same spatial resolution. These two datasets separately undergo NMF (e.g., at 508 and 516) to extract abundance maps (e.g., 510, 518) which are then paired through correlation (e.g., at 520), e.g., through CCA establishing the cross-correlation matrix G. This matrix can be further used to reconstruct either of the dataset. The correlation or the cross-correlation matrix G allows to infer MALDI-type molecular mass spectra by ToF-SIMS dataset at original high spatial resolution. For example, ToF-SIMS dataset (e.g., at 522) can be transformed by the NMF (e.g., at 524) using previously calculated endmembers (e.g., at 508), then a trained correlation transformation (e.g., at 520), e.g., CCA transformation, infers the MALDI abundance maps (e.g., at 528) via multiplication by the matrix G or correlation, which is followed by an inverse NMF (e.g., at 530, e.g., inverse of NMF at 516) which generates a MALDI-type mass spectral array at ToF-SIMS imaging resolution (e.g., at 532).

Figure 6:
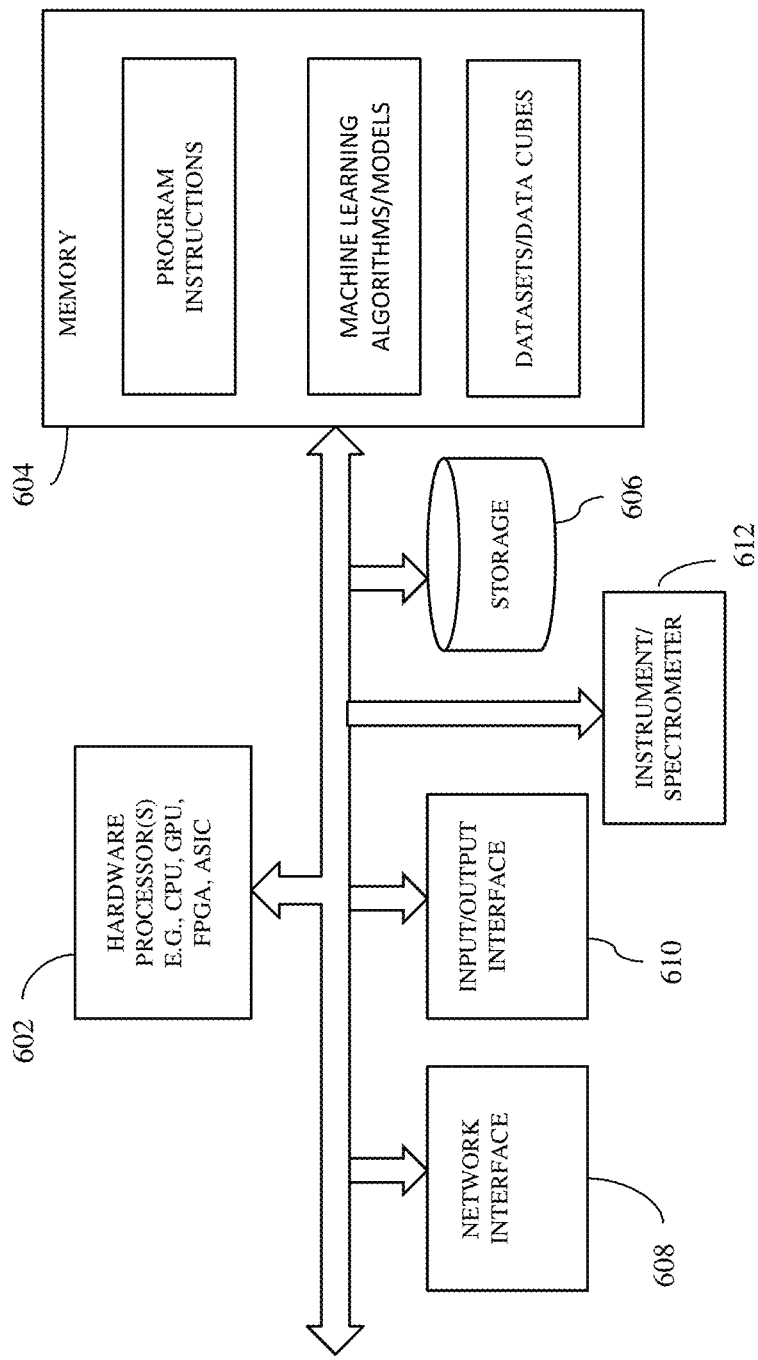
FIG. 6 is a diagram showing components of a system in one embodiment that can train a machine learning model for correlative multimodal chemical imaging.

FIG. 6 is a diagram showing components of a system in one embodiment that can train a machine learning model for correlative multimodal chemical imaging. One or more hardware processors 602 such as a central processing unit (CPU), a graphic process unit (GPU), and/or a Field Programmable Gate Array (FPGA), an application specific integrated circuit (ASIC), and/or another processor, may be coupled with a memory device 604, and generate a prediction model for generating an image of desired resolution. A memory device 604 may include random access memory (RAM), read-only memory (ROM) or another memory device, and may store data and/or processor instructions for implementing various functionalities associated with the methods and/or systems described herein. One or more processors 602 may execute computer instructions stored in memory 604 or received from another computer device or medium. A memory device 604 may, for example, store instructions and/or data for functioning of one or more hardware processors 602, and may include an operating system and other program of instructions and/or data. One or more hardware processors 602 may receive input including spectral datasets. Such input data may be stored in a storage device 606 or received via a network interface 608 from a remote device, and may be temporarily loaded into a memory device 604 for building or generating the prediction model. One or more hardware processors 602 can also be coupled with an instrument 612, e.g., including a spectrometer, for example, via a device interface. In another aspect, raw imaging signal data can be received or acquired from one or more instruments 612 having one or more spectrometers, and formatted for use by at least one processor 602. At least one hardware processor 602 may generate a prediction model that can generate an image of desired resolution. For instance, a hardware processor may co-register spectral inputs, perform dimensionality reduction, and identify physical relations between channels using machine learning. The learned or trained prediction model may be stored on a memory device 604, for example, for running by one or more hardware processors 602. One or more hardware processors 602 may also use the model to generate or reconstruct an image, e.g., reconstruct molecular mass spectra at high resolution. One or more hardware processors 602 may be coupled with interface devices such as a network interface 608 for communicating with remote systems, for example, via a network, and an input/output interface 610 for communicating with input and/or output devices such as a keyboard, mouse, display, and/or others.

Various aspects of the present disclosure may be embodied as a program, software, or computer instructions embodied or stored in a computer or machine usable, readable or executable medium, which causes the computer or machine to perform the steps of the method when executed on the computer, processor, and/or machine. For instance, a program storage device readable by a machine, tangibly embodying a program of instructions executable by the machine to perform various functionalities and methods described in the present disclosure may be provided.

The system and method of the present disclosure may be implemented and run on a general-purpose computer or special-purpose computer system. The computer system may be any type of known or will be known systems and may include a hardware processor, memory device, a storage device, input/output devices, internal buses, and/or a communications interface for communicating with other computer systems in conjunction with communication hardware and software, etc.

In an embodiment, the present invention may be embodied as a computer program product that may include a computer readable storage medium (or media) and/or a computer readable storage medium. Such computer readable storage medium may store computer readable program instructions for causing a processor to carry out one or more methodologies described here. In one embodiment, the computer readable storage medium includes a tangible device that can retain and store instructions for use by an instruction execution device. Examples of the computer readable storage medium may include, but is not limited to, an electronic storage device, a magnetic storage device, an optical storage device, an electromagnetic storage device, a semiconductor storage device, or any suitable combination thereof, for example, such as a computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, but not limited to only those examples.

The terms "computer system" and "computer network" as may be used in the present application may include a variety of combinations of fixed and/or portable computer hardware, software, peripherals, mobile, and storage devices. The computer system may include a plurality of individual components that are networked or otherwise linked to perform collaboratively, or may include one or more stand-alone components. The hardware and software components of the computer system of the present application may include and may be included within fixed and portable devices such as mobile phone, tablet, smartphone, desktop, laptop, and/or server. A module may be a component of a device, software, program, or system that implements some "functionality", which can be embodied as software, hardware, firmware, electronic circuitry, or etc.

The terminology used herein is for the purpose of describing particular embodiments only and is not intended to be limiting of the invention. As used herein, the singular forms "a", "an" and "the" are intended to include the plural forms as well, unless the context clearly indicates otherwise. As used herein, the term "or" is an inclusive operator and can mean "and/or", unless the context explicitly or clearly indicates otherwise. It will be further understood that the terms "comprise", "comprises", "comprising", "include", "includes", "including", and/or "having," when used herein, can specify the presence of stated features, integers, steps, operations, elements, and/or components, but do not preclude the presence or addition of one or more other features, integers, steps, operations, elements, components, and/or groups thereof. As used herein, the phrase "in an embodiment" does not necessarily refer to the same embodiment, although it may. As used herein, the phrase "in one embodiment" does not necessarily refer to the same embodiment, although it may. As used herein, the phrase "in another embodiment" does not necessarily refer to a different embodiment, although it may. Further, embodiments and/or components of embodiments can be freely combined with each other unless they are mutually exclusive.

The corresponding structures, materials, acts, and equivalents of all means or step plus function elements, if any, in the claims below are intended to include any structure, material, or act for performing the function in combination with other claimed elements as specifically claimed. The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiment was chosen and described in order to best explain the principles of the invention and the practical application, and to enable others of ordinary skill in the art to understand the invention for various embodiments with various modifications as are suited to the particular use contemplated.

What is claimed is:

1. A system comprising:
an instrument configured to:
acquire first-type spectral image data, the first-type spectral image data corresponding to a first-type spectral-data cube having two spatial dimensions of first-spatial resolution and one spectral dimension, wherein each point in the two spatial dimensions has an associated first-type spectrum, the first-type spectral-data cube indicative of one or more constitutive molecular compounds of a sample and their abundance on the sample's surface corresponding to the two spatial dimensions;
acquire second-type spectral image data, the second-type spectral image data corresponding to a second-type spectral-data cube having two spatial dimensions of second-spatial resolution and one spectral dimension, wherein each point in the two spatial dimensions has an associated second-type spectrum, the second-type spectral-data cube indicative of fragments of the one or more constitutive molecular compounds of the sample and their abundance on the sample's surface corresponding to the two spatial dimensions, the second-spatial resolution having higher-spatial resolution than the first-spatial resolution;
and
a processor configured to train a machine learning model to generate a spectral image, by:
co-registering the first-type spectral-data cube and the second-type spectral data cube and spatially down-sampling the second-type spectral-data cube to the first-spatial resolution of the received first-type spectral-data cube, and,
transforming the first-type spectral-data cube into abundance maps of first components, wherein a first component of the first components includes one or more molecular compounds that coexist together spatially,
transforming the second-type spectral-data cube into abundance maps of second components, wherein a second component of the second components includes one or more fragments of one or more molecular compounds that coexist together spatially, and
spatially correlating the first components' abundance maps with the second components' abundance maps, and storing resulting set of correlations as learned parameters of the machine learning model;
the processor further configured to:
receive a new second-type spectral-data cube having the second-spatial resolution; and
generate a spectral image, based on running the trained machine learning model, the spectral image represented by a first-type spectral data cube having the second-spatial resolution and corresponding to the newly received second-type spectral-data cube.

2. The system of claim 1, wherein the instrument comprises a spectrometer capable of
acquiring ToF-SIMS images having second-spatial resolution.

3. The system of claim 2, wherein the instrument comprises another spectrometer capable of acquiring MALDI-MS images having first-spatial resolution.

4. The system of claim 2, wherein the spectrometer is further capable of acquiring MALDI-MS images having first-spatial resolution.

5. The system of claim 1, wherein the processor is configured to spatially correlate the first components' abundance maps with the second components' abundance maps by performing a canonical correlation analysis to determine the resulting set of correlations.

6. The system of claim 1, wherein the processor is configured to spatially down-sample the second-type spectral-data cube to the first-spatial resolution of the received first-type spectral-data cube by linearly interpolating the received second-type spectral-data cube to the first-spatial resolution.

7. The system of claim 1, wherein the processor is configured to co-registerer the first-type spectral-data cube and the second-type spectral data cube by spatially linking the first-type spectral cube and the second-type spectral data cube by aligning coordinates of the two spatial dimensions of the first-type spectral cube and the second-type spectral data cube.

8. The system of claim 7, wherein the processor is configured to align the coordinates of the two spatial dimensions of the first-type spectral cube and the second-type spectral data cube based on locating a marker appearing on the first-type spectral cubes.

9. The system of claim 1, wherein the processor is configured to cause a display of the generated first-type spectral data cube having the second-spatial resolution as a spectral image.

10. The system of claim 1, wherein to generate, based on the trained machine learning model, the first-type spectral-data cube having second-spatial resolution and corresponding to the newly received second-type spectral-data cube, the processor is configured to:
transform the new second-type spectral-data cube having the second-spatial resolution into second-spatial resolution abundance maps of the second components,
determine second-spatial resolution abundance maps of the first components from the stored resulting set of correlations and the second-spatial resolution abundance maps of the second components, and
recover the first-type spectral-data cube having second-spatial resolution from the second-spatial resolution abundance maps of the first components.

11. The system of claim 10, wherein the instrument includes the processor.

12. The system of claim 10, wherein the processor is configured to transform the first-type spectral-data cube having first-spatial resolution into abundance maps of first components by
decomposing first spectra of the first-type spectral-data cube as linear combinations of spectra corresponding to the first components and determining the first components' abundance maps as the first spectra's weights associated with the first components, and
wherein the processor is configured to transform the second-type spectral-data cube into abundance maps of second components by
decomposing second spectra of the second-type spectral-data cube as linear combinations of spectra corresponding to the second components and determining the second components' abundance maps as the second spectra's weights associated with the second components.

13. The system of claim 12, wherein the processor is configured to transform the first-type spectral-data cube into abundance maps of first components by
performing a non-negative matrix factorization (NMF) on the received first-type spectral-data cube, and
wherein the processor is configured to transform the second-type spectral-data cube into abundance maps of second components by
performing a non-negative matrix factorization (NMF) on the second-type spectral-data cube.

14. The system of claim 10, wherein to transform the new second-type spectral-data cube having the second-spatial resolution into second-spatial resolution abundance maps of the second components, the processor is configured to use the second components determined from the transforming the second-type spectral-data cube into abundance maps of second components, the transforming performed with a non-negative matrix factorization (NMF) on the second-type spectral-data cube.

15. The system of claim 10, wherein to recover the first-type spectral-data cube having second-spatial resolution from the second-spatial resolution abundance maps of the first components, the processor is configured to perform an inverse of the transformation performed on the first-type spectral-data cube to transform the first-type spectral-data cube into the abundance maps of the first components.

16. A computer-implemented method comprising:
receiving a first-type spectral-data cube having two spatial dimensions of first-spatial resolution and one spectral dimension, wherein each point in the two spatial dimensions has an associated first-type spectrum, wherein the first-type spectral-data cubes is indicative of one or more constitutive molecular compounds of a sample and their abundance on the sample's surface corresponding to the two spatial dimensions;
receiving a second-type spectral-data cube having two spatial dimensions of second-spatial resolution and one spectral dimension, wherein each point in the two spatial dimensions has an associated second-type spectrum, wherein the second-type spectral-data cube is indicative of fragments of the one or more constitutive molecular compounds of the sample and their abundance on the sample's surface corresponding to the two spatial dimensions, the second-spatial resolution having higher-spatial resolution than the first-spatial resolution;
training a machine learning model to generate a spectral image, by:
co-registering the first-type spectral-data cube and the second-type spectral data cube and spatially down-sampling the second-type spectral-data cube to the first-spatial resolution of the received first-type spectral-data cube,
transforming the first-type spectral-data cube into abundance maps of first components, wherein a first component of the first components includes one or more molecular compounds that coexist together spatially,
transforming the second-type spectral-data cube into abundance maps of second components, wherein a second component of the second components includes one or more fragments of one or more molecular compounds that coexist together spatially, and
spatially correlating the first components' abundance maps with the second components' abundance maps, and storing resulting set of correlations as learned parameters of the machine learning model;
receiving a new second-type spectral-data cube having the second-spatial resolution; and
generating a spectral image, based on running the trained machine learning model, the spectral image represented by a first-type spectral data cube having the second-spatial resolution and corresponding to the newly received second-type spectral-data cube.

17. The method of claim 16, wherein the first-type spectral-data cube is a MALDI-MS image, and the first-type spectrum is MALDI-MS spectrum, and the second-type spectral-data cube is ToF-SIMS image, and the second-type spectrum is ToF-SIMS spectrum.

18. The method of claim 16, wherein the second-spatial resolution corresponds to 0.05-1 µm and the first-spatial resolution corresponds to 5-50 µm, per point in the two spatial dimension.

19. The method of claim 16, wherein transforming the first-type spectral-data cube having first-spatial resolution into abundance maps of first components comprises decomposing first spectra of the first-type spectral-data cube as linear combinations of spectra corresponding to the first components and determining the first components' abundance maps as the first spectra's weights associated with the first components, and transforming the second-type spectral-data cubes into abundance maps of second components comprises decomposing second spectra of the second-type spectral-data cube as linear combinations of spectra corresponding to the second components and determining the second components' abundance maps as the second spectra's weights associated with the second components.

20. The method of claim 19, wherein the transforming of the first-type spectral-data cube into abundance maps of first components comprises performing a non-negative matrix factorization (NMF) on the received first-type spectral-data cube, and
transforming the second-type spectral-data cube into abundance maps of second components comprises performing a non-negative matrix factorization (NMF) on the second-type spectral-data cube.

21. The method of claim 16, wherein the spatially correlating of the first components' abundance maps with the second components' abundance maps comprises performing a canonical correlation analysis to determine the resulting set of correlations.

22. The method of claim 16, wherein the spatially down-sampling the second-type spectral-data cube to the first-spatial resolution of the received first-type spectral-data cube includes linearly interpolating the received second-type spectral-data cube to the first-spatial resolution.

23. The method of claim 16, wherein the co-registering of the first-type spectral-data cube and the second-type spectral data cube comprises spatially linking the first-type spectral cube and the second-type spectral data cube by aligning coordinates of the two spatial dimensions of the first-type spectral cube and the second-type spectral data cube.

24. The method of claim 16, further comprising causing a display of the generated first-type spectral data cube having the second-spatial resolution as a spectral image.

25. The method of claim 16, wherein the generating, based on the trained machine learning model, the first-type spectral-data cube having second-spatial resolution and corresponding to the newly received second-type spectral-data cube, comprises:
transforming the new second-type spectral-data cube having the second-spatial resolution into second-spatial resolution abundance maps of the second components,
determining second-spatial resolution abundance maps of the first components from the stored resulting set of correlations and the second-spatial resolution abundance maps of the second components, and
recovering the first-type spectral-data cube having second-spatial resolution from the second-spatial resolution abundance maps of the first components.

26. The method of claim 25, wherein the transforming of the new second-type spectral-data cube having the second-spatial resolution into second-spatial resolution abundance maps of the second components, comprises using the second components determined from the transforming the second-type spectral-data cube into abundance maps of second components, the transforming performed with a non-negative matrix factorization (NMF) on the second-type spectral-data cube.

27. The method of claim 25, wherein the recovering of the first-type spectral-data cube having second-spatial resolution from the second-spatial resolution abundance maps of the first components, comprises performing an inverse of the transformation performed on the first-type spectral-data cube to transform the first-type spectral-data cube into the abundance maps of the first components.

28. A computer readable storage medium storing a program of instructions executable by a machine to perform a method of:
- receiving a first-type spectral-data cube having two spatial dimensions of first-spatial resolution and one spectral dimension, wherein each point in the two spatial dimensions has an associated first-type spectrum, wherein the first-type spectral-data cubes is indicative of one or more constitutive molecular compounds of a sample and their abundance on the sample's surface corresponding to the two spatial dimensions;
- receiving a second-type spectral-data cube having two spatial dimensions of second-spatial resolution and one spectral dimension, wherein each point in the two spatial dimensions has an associated second-type spectrum, wherein the second-type spectral-data cube is indicative of fragments of the one or more constitutive molecular compounds of the sample and their abundance on the sample's surface corresponding to the two spatial dimensions, the second-spatial resolution having higher-spatial resolution than the first-spatial resolution;
- training a machine learning model to generate a spectral image, by:
  - co-registering the first-type spectral-data cube and the second-type spectral data cube and spatially downsampling the second-type spectral-data cube to the first-spatial resolution of the received first-type spectral-data cube,
  - transforming the first-type spectral-data cube into abundance maps of first components, wherein a first component of the first components includes one or more molecular compounds that coexist together spatially,
  - transforming the second-type spectral-data cube into abundance maps of second components, wherein a second component of the second components includes one or more fragments of one or more molecular compounds that coexist together spatially, and
  - spatially correlating the first components' abundance maps with the second components' abundance maps, and storing resulting set of correlations as learned parameters of the machine learning model;
- receiving a new second-type spectral-data cube having the second-spatial resolution; and
- generating a spectral image, based on running the trained machine learning model, the spectral image represented by a first-type spectral data cube having the second-spatial resolution and corresponding to the newly received second-type spectral-data cube.

29. A system comprising:
- a processor; and
- a memory device coupled with the processor;
- the processor configured to at least:
  - receive a first-type spectral-data cube having two spatial dimensions of first-spatial resolution and one spectral dimension, wherein each point in the two spatial dimensions has an associated first-type spectrum, wherein the first-type spectral-data cubes is indicative of one or more constitutive molecular compounds of a sample and their abundance on the sample's surface corresponding to the two spatial dimensions;
  - receive a second-type spectral-data cube having two spatial dimensions of second-spatial resolution and one spectral dimension, wherein each point in the two spatial dimensions has an associated second-type spectrum, wherein the second-type spectral-data cube is indicative of fragments of the one or more constitutive molecular compounds of the sample and their abundance on the sample's surface corresponding to the two spatial dimensions, the second-spatial resolution having higher-spatial resolution than the first-spatial resolution;
  - training a machine learning model to generate a spectral image, by:
    - co-registering the first-type spectral-data cube and the second-type spectral data cube and spatially establishing one-to-one pairing of the spectra of the first-type spectral-data cube and the second-type spectral data cube,
    - transforming the first-type spectral-data cube into abundance maps of first components, wherein a first component of the first components includes one or more molecular compounds that coexist together spatially,
    - transforming the second-type spectral-data cube into abundance maps of second components, wherein a second component of the second components includes one or more fragments of one or more molecular compounds that coexist together spatially,
  - spatially correlating the first components' abundance maps with the second components' abundance maps, and storing resulting set of correlations as learned parameters of the machine learning model, and
  - receive a new second-type spectral-data cube having the second-spatial resolution; and
  - generate the spectral image, based on running the trained machine learning model, the spectral image represented by a first-type spectral data cube having the second-spatial resolution and corresponding to the newly received second-type spectral-data cube.

* * * * *